(12) United States Patent
Gopinath

(10) Patent No.: US 12,127,874 B2
(45) Date of Patent: Oct. 29, 2024

(54) SYSTEMS AND METHODS OF COMBINED IMAGING

(71) Applicant: LightLab Imaging, Inc., Westford, MA (US)

(72) Inventor: Ajay Gopinath, Bedford, MA (US)

(73) Assignee: LightLab Imaging, Inc., Westford, MA (US)

( * ) Notice: Subject to any disclaimer, the term of this patent is extended or adjusted under 35 U.S.C. 154(b) by 0 days.

(21) Appl. No.: 17/025,473

(22) Filed: Sep. 18, 2020

(65) Prior Publication Data

US 2021/0085275 A1    Mar. 25, 2021

Related U.S. Application Data

(60) Provisional application No. 62/902,948, filed on Sep. 19, 2019.

(51) Int. Cl.
| | |
|---|---|
| *A61B 6/00* | (2024.01) |
| *A61B 5/33* | (2021.01) |
| *A61B 6/50* | (2024.01) |
| *A61B 90/00* | (2016.01) |

(52) U.S. Cl.
CPC .............. *A61B 6/5235* (2013.01); *A61B 5/33* (2021.01); *A61B 6/487* (2013.01); *A61B 6/504* (2013.01); *A61B 6/507* (2013.01); *A61B 6/541* (2013.01); *A61B 90/39* (2016.02); *A61B 2090/3966* (2016.02)

(58) Field of Classification Search
CPC .. A61B 90/00; A61B 5/00; A61B 6/00; A61B 6/5235
See application file for complete search history.

(56) References Cited

U.S. PATENT DOCUMENTS

| | | |
|---|---|---|
| 2006/0241465 A1 | 10/2006 | Huennekens et al. |
| 2008/0306766 A1 | 12/2008 | Ozeki et al. |
| 2010/0049038 A1* | 2/2010 | Florent ................. A61B 6/481 600/425 |
| 2010/0074504 A1 | 3/2010 | Bruijns et al. |
| 2011/0319752 A1 | 12/2011 | Steinberg et al. |

(Continued)

FOREIGN PATENT DOCUMENTS

| | | |
|---|---|---|
| JP | 2008-301984 A | 12/2008 |
| JP | 2011-206336 A | 10/2011 |

(Continued)

OTHER PUBLICATIONS

International Search Report with Written Opinion for Application No. PCT/US2020/051501 mailed Dec. 14, 2020, 14 pages.

(Continued)

*Primary Examiner* — Angela M Hoffa
*Assistant Examiner* — Younhee Choi
(74) *Attorney, Agent, or Firm* — Lerner David LLP

(57) ABSTRACT

Systems and methods are provided for the combination and display of both live and non-live patient images. The features described include collecting angiographic image data, and correlating angiographic image frames to time-varying data relating to the patient's heart cycle. This time-varying data may then be compared with the patient's live heart cycle data so that the collected angiographic image frames can be interlaced within a display of live fluoroscopic images of the patient.

22 Claims, 10 Drawing Sheets

Sync Live Fluoro data with OCT-Angio-Coreg.

(56) References Cited

U.S. PATENT DOCUMENTS

| | | | | |
|---|---|---|---|---|
| 2013/0101084 A1* | 4/2013 | Shimizu | ............... | A61B 6/481 |
| | | | | 378/42 |
| 2013/0136332 A1* | 5/2013 | Uehara | ............... | A61B 6/50 |
| | | | | 382/132 |
| 2014/0270436 A1* | 9/2014 | Dascal | ............... | A61B 6/463 |
| | | | | 382/130 |
| 2014/0328462 A1 | 11/2014 | Uehara et al. | | |
| 2015/0139388 A1 | 5/2015 | Liu | | |
| 2015/0313466 A1* | 11/2015 | Yoshida | ............... | A61B 5/026 |
| | | | | 600/425 |
| 2016/0335742 A1 | 11/2016 | Yim et al. | | |
| 2017/0245822 A1 | 8/2017 | Vaillant et al. | | |
| 2018/0153408 A1* | 6/2018 | Yao | ............... | A61B 5/748 |
| 2018/0330507 A1* | 11/2018 | Schormans | ............... | A61B 5/318 |
| 2019/0087955 A1 | 3/2019 | Takahashi et al. | | |

FOREIGN PATENT DOCUMENTS

| | | | |
|---|---|---|---|
| JP | 2012-245221 A | 12/2012 | |
| JP | 2014-028124 A | 2/2014 | |
| JP | 2016-516466 A | 6/2016 | |
| KR | 20190118454 A | * 10/2019 | |

OTHER PUBLICATIONS

Phillips, "Azurion Release 1.1 Instructions for Use", Philips Healthcare 4522 203 5211. (Dec. 2016). 362 pgs.

Canadian Office Action issued in Appln. No. 3151618 mailed Jun. 15, 2023 (3 pages).

EP Office Action issued in Appln. No. 20786363.0 mailed Nov. 29, 2023 (5 pages).

Office Action issued in Japanese Appln. No. 2022-517847 mailed Apr. 5, 24 (5 pages).

Nobori, Kunio, Imagawa, Taro, Hideto Motomura, Azuma, Takeo, "High-Resolution and High-Frame-Rate Video Reconstruction from Color-Separated Video with Different Spatio-Temporal Resolutions by Simultaneous Estimation of Motion and Reconstructed Video", The Journal of the Institute of Image ElectronicsEngineers of Japan, 2013, and vol. 42 No. 4, pp. 527-535, URL, https://www.jstage.jst.go.jp/article/ileej/42/4/42_527/_pdf (English Abstract only).

JP Search Report for Application No. 2022-517847 dated Feb. 5, 2024. 15 pgs.

* cited by examiner

SYSTEMS AND METHODS OF COMBINED IMAGING

CROSS-REFERENCE TO RELATED APPLICATIONS

The present application claims the benefit of the filing date of U.S. Provisional Patent Application No. 62/902,948 filed Sep. 19, 2019, the disclosure of which is hereby incorporated herein by reference.

FIELD

The disclosure relates generally to the field of vascular system imaging and data collection systems and methods. In particular, the disclosure relates to methods of providing live x-ray images such as fluoroscopic images in combination with co-registered angiography frames.

BACKGROUND

Coronary artery disease is one of the leading causes of death worldwide. The ability to better diagnose, monitor, and treat coronary artery diseases can be of life saving importance. During various medical and technical personnel are viewing multiple sources of information including angiography images and live fluoroscopy images as part of stent planning or stent delivery. Switching between these two sources of data can be fatiguing and often requires that such personnel hold images and other data associations in their mind as they switch from a changing fluoroscopic view to an angiography as part of stent planning and delivery A need therefore exists for systems, methods, and devices that provide useful diagnostic information and improve imaging for planning and for cardiovascular procedures.

The present disclosure addresses these challenges and others.

SUMMARY

In part, the disclosure relates to a system and method of co-registering live fluoroscopy image data with angiography image data. The method includes collecting, during a first imaging session, a first set of time varying data that corresponds to heart cycle at one or more points in time, wherein the first imaging session comprises angiography imaging of a subject to generate a set of angiography frames; identifying angiography frames that correspond to a first subset of the time varying data; tracking or collecting, during a second imaging session, a second set of time varying data that corresponds to heart cycle at one or more points in time, wherein the second imaging session comprises live fluoroscopic imaging of a subject to generate a set of live fluoroscopy frames angiography frames; correlating the first set of time varying data with the second set of time varying data to identify angiography frames corresponding to live fluoroscopy frames; and displaying a first set of one or more live fluoroscopy frames and one or more angiography frames corresponding to a second set of one or more live fluoroscopy frames.

Various sources and streams of intravascular and peripheral vascular image data can be combined and interlaced as disclosed herein. Further, various cardiovascular signals and rhythms can be used to support co-registering two or more imaging moalities and then combing one or both co-registered imaging modalities with live image data such as fluoroscopy, cines, or other live images used in the catheterization laboratory ("cath lab"). One or more devices can display one or more user interfaces and intravascular data or other information derived from such data. The intravascular data can be obtained using IVUS or OCT based data collection systems and probes or other imaging modalities. The methods can be implemented using one or more computing devices and memory storages that receive intravascular data and user inputs via a graphic user interface (GUI) and include one or more image processing and frame selection software components. The computing devices can be microprocessors, ASICs or other processors suitable for use with an intravascular imaging system.

In part, the disclosure relates to systems and methods to evaluate and deploy stents using a combination of live fluoroscopy frames and angiography frames. The combination of interlaced frames supports artherectomy, stenting, and balloon-based treatments as enhanced by imaging, analysis and diagnostic systems and combinations of the foregoing. The disclosure provides for a systems and methods of acquiring, by one or more processors, a first set of subject images captured during a first time period and a first set of time-varying data that corresponds to a heart cycle of the subject during the first time period; correlating, by the one or more processors, subsets of the first set of subject images with subsets of the first set of time-varying data; acquiring, by the one or more processors, a second set of subject images captured during a second time period and a second set of time-varying data that corresponds to the heart cycle of the subject acquired during the second time period; correlating, by the one or more processors, the first set of time-varying data with the second set of time-varying data; identifying, by the one or more processors, one or more image frames from the first set of subject images that corresponds to a subset of the second set of time-varying data; providing for display, by the one or more processors, the identified one or more image frames from the first set of subject images interlaced with a plurality of image frames from the second set of subject images.

In accordance with the disclosure, the first set of subject images may be angiographic images and the second set of subject images may be fluoroscopic images. In addition, the fluoroscopic images may be live images of the subject and the second set of time-varying data may be live heart cycle data for the subject.

In accordance with another aspect of the disclosed systems and methods, the first set of time-varying data and the second set of time-varying data may include aortic (AO) pressure values and/or ECG values. In addition, the first time period may comprise simultaneously intravascularly imaging the subject using an intravascular probe, such as an OCT or IVUS probe, having one or more opaque markers, wherein intravascularly imaging the subject generates a set of intravascular image frames. In addition, the system may be configured to co-register the intravascular image frames and the first set of subject image. The system may also be configured to display one or more intravascular image frames or a subset thereof corresponding to one or more live angiography frames.

The disclosed system may also be configured to display to a user the identified one or more image frames from the first set of subject images interlaced with a plurality of image frames from the second set of subject images. The interlacing of image frames by include replacing one or more image frames from the second set of subject images with one or more image frames from the first set of subject images. In accordance with aspects of the disclosure, one or more image frames from the second set of subject images and the one or more image frames from the first set of subject images may each be captured during a corresponding portion of the patient's heart cycle. The system may also be configured to display the identified one or more image frames from the first set of subject images interlaced with a plurality of image frames from the second set of subject images by inserting the identified one or more image frames from the first set of subject images between image frames from the second set of subject images.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation. Further, the various software-based tools to address medical imaging problems and other related challenges and problems and parts of the foregoing can be used for medical applications and other applications for displaying information relating to stents, blood vessels, and two and three-dimensional views thereof without limitation. Other features and advantages of the disclose embodiments will be apparent from the following description and accompanying drawings.

Although, the disclosure relates to different aspects and embodiments and other features as recited and depicted herein, it is understood that the each of the foregoing disclosed herein can be integrated together as a whole or in part, as appropriate. Thus, each embodiment disclosed herein can be incorporated in each of the aspects to varying degrees as appropriate for a given implementation. Further, the various stent expansion diagnostic tools described herein can be used with various imaging modalities.

Other features and advantages of the disclosed embodiments will be apparent from the following description and accompanying drawings.

DETAILED DESCRIPTION

Figure 1A:
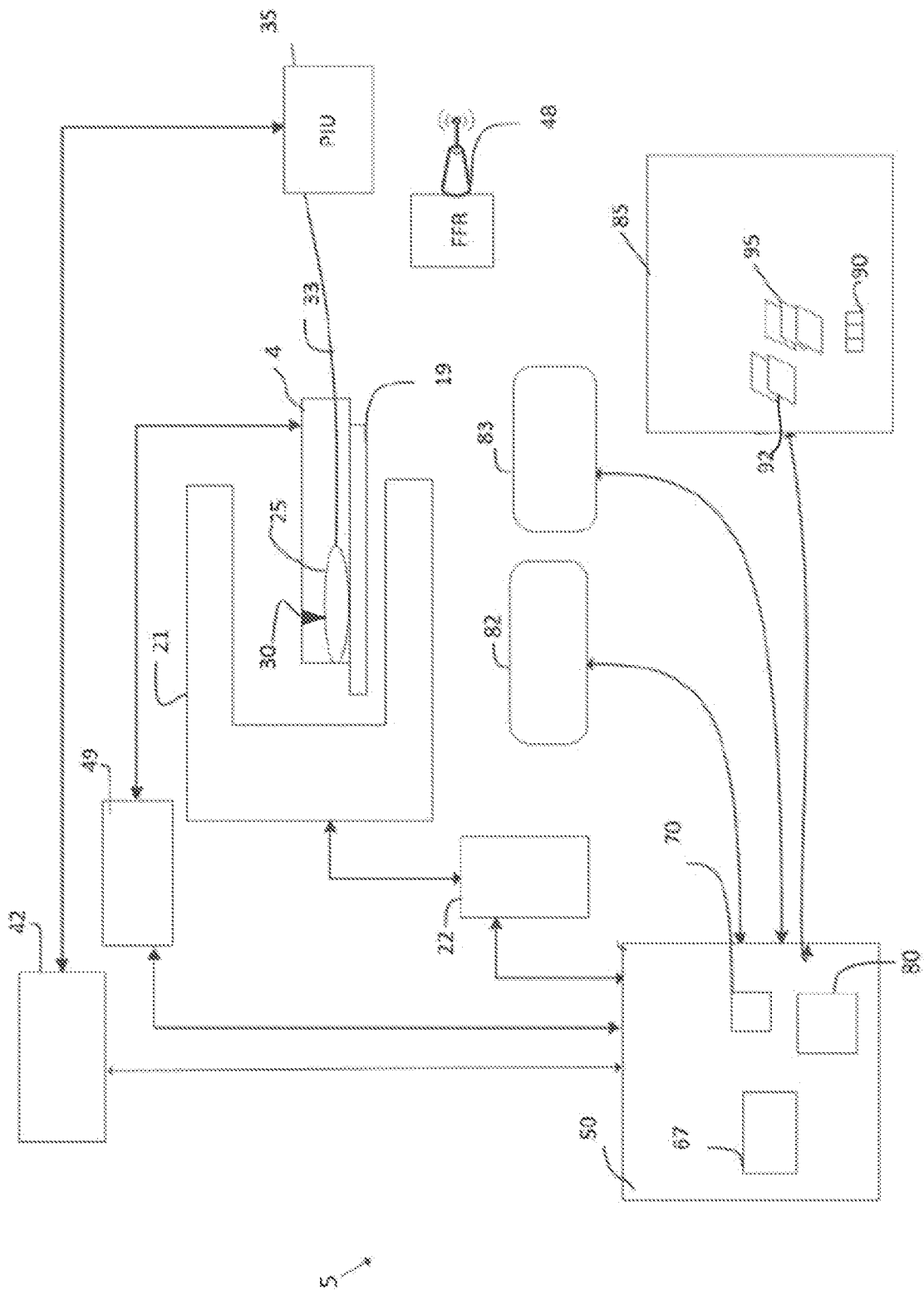
FIG. 1A shows a schematic diagram of an imaging and data collection system in accordance with aspects of the disclosure.

In part, the disclosure relates to systems and methods that use cardiovascular system timing parameters, and or signals such as ECG and pressure signals, such as aortic pressure signals, to identify the angiography frames that correspond to parts of the heart cycle. The dicrotic notch and other timing indicia such as those used to identify systole and diastole can be used. Further, the disclosed systems and methods may identify angiography frames corresponding to a current fluoroscopy image based on real time correlation with such signals and/or timing parameters.

In one embodiment, for each live fluoroscopy frame, the corresponding angiography frame is identified based on signal or timing parameter correlation, such as through ECG correlation. Further, in some embodiments, intravascular probe markers, such as radio opaque markers are used under angiography and correlated therewith as part of an intravascular imaging sessions such as through optical coherence tomography (OCT) or intravascular imaging is intravascular ultrasound ("IVUS") imaging. In this way, the intravascular imaging (such as OCT or IVUS) facilitates angiography correlation.

OCT is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a user to diagnose as well as monitor the progression of coronary artery disease. Another form of intravascular imaging is intravascular ultrasound ("IVUS") imaging, which uses high-frequency sound waves to create intravascular images.

OCT/IVUS imaging of portions of a patient's body provides a useful diagnostic tool for doctors and others. For example, imaging of coronary arteries by intravascular OCT/IVUS may reveal the location of a narrowing or stenosis. This information helps cardiologists to choose between an invasive coronary bypass surgery and a less invasive catheter-based procedure such as angioplasty or stent delivery. Although a popular option, stent delivery has its own associated risks.

In one embodiment, the angiography and live fluoroscopy co-registration can be combined with the foregoing to allow intravascular markers and intravascular image data or parameters to be overlaid with or co-registered with live fluoroscopy. Stent detection, stent expansion, side branches, and other image data detected based on collected intravascular datasets can be linked to or displayed relative to live fluoroscopy images and angiography images as a result of the co-registration between and among the three image datasets.

These various sets of data, angiography, intravascular imaging (OCT/IVUS), and live fluoroscopy can be combined, interlaced, used, juxtaposed or integrated in various ways to present combinations or co-registered data to end user. Further, in various embodiments, the disclosure relates to method of reducing contrast solution usage by interlacing angiography frames with live fluoroscopy, such that fewer angiography frames are used and thus less contrast solution is necessitated.

Using angiography images, fluoroscopy data, and intravascular data, and other imaging modalities in support of cardiovascular diagnosis and stenosis treatment is of great value if it can be done on an expedited timescale and in a manner that helps the end user. Dealing with various competing obstacles to these goals represents important technical challenges. The use of co-registration data and signals, such as AO, EKG, systole transitions, diastole transitions, and others along with the generation of various interlaced, static, combined, and fused datasets, including streams of data that has a live subset of frames and a stored, historic, or otherwise non-live subset of frames can be used in various embodiments.

In part, the disclosure relates to systems and methods of fusing angiography co-registration images and/or data with live fluoroscopy. Further, the disclosure relates to systems and methods to combine angiography (angio) co-registration (co-reg or registration or reg) information with one or more live fluoroscopy feeds.

Figure 1B:
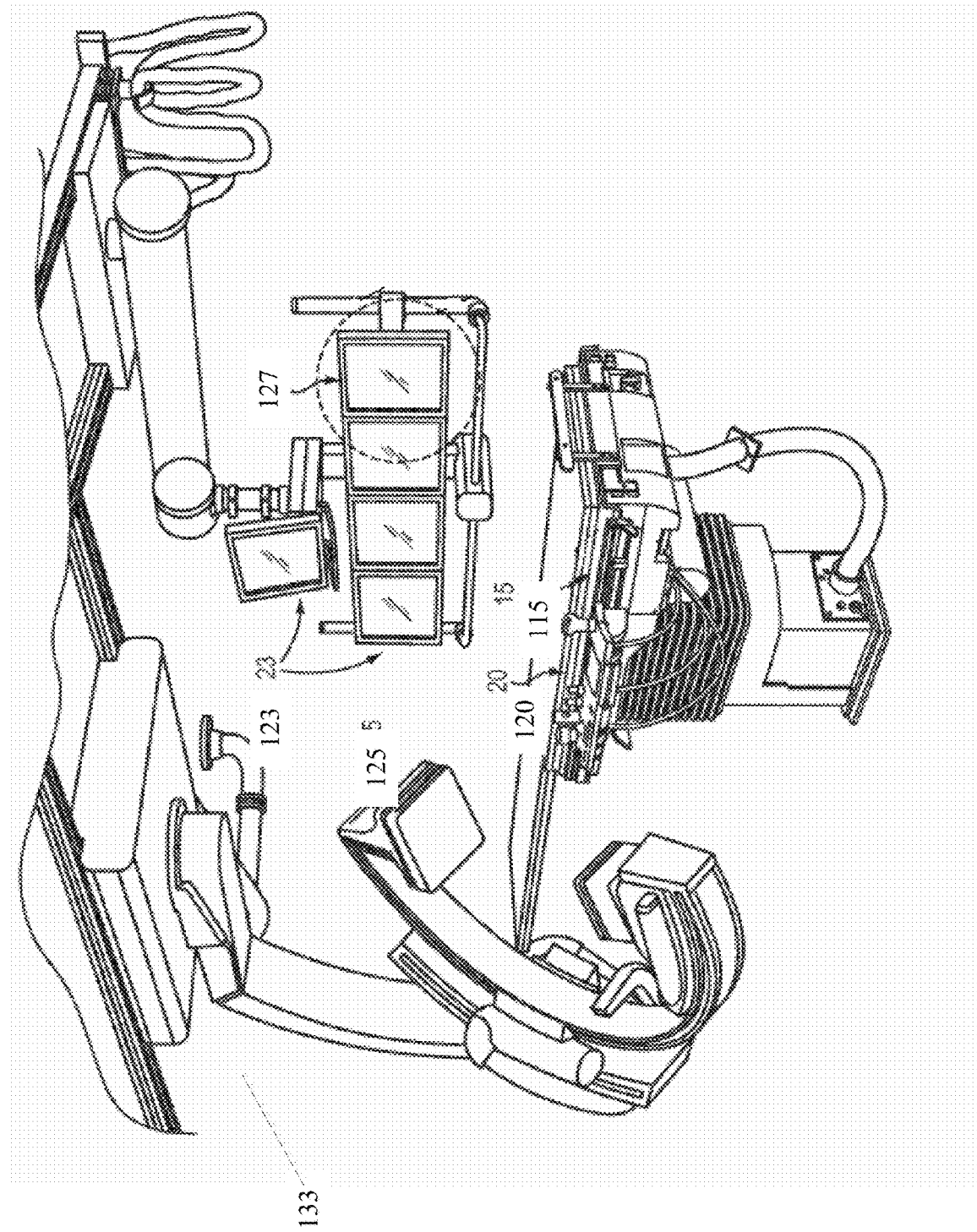
FIG. 1B shows an exemplary operation configuration of an embodiment in accordance with aspects of the disclosure.

FIGS. 1A and 1B show a schematic diagram of an imaging and data collection system suitable for imaging arteries, stents, and other cardiovascular system components and synchronizing live data with data obtained during co-registration of angiography data and intravascular data s in accordance with an illustrative embodiment of the disclosure. In one embodiment, a fluoroscopy feed is obtained from a C-Arm or other fluoroscopic imaging device or system such as shown in FIGS. 1A and 1B. In various embodiments, the imaging systems, devices, and subsystems disclosed are suitable for use in a cath lab. This will provide direct guidance for physicians seeking to place stents and devices in locations that they had planned in an OCT/IVUS-Angio co-registration system.

The systems and methods disclosed herein solve various technical challenges that physicians and other cath lab personnel must deal with during various procedures. For example, a physician engaged in stent planning on one screen, such as an angiography screen on one display 127, 82, or others and simultaneously is pushing a stent along and looking to another screen 133 that may be far away and relaying live fluoroscopy data while trying to mentally combining this information is incredibly taxing. If other data, such as intravascular data or pressure data is being provided on different screens it adds further to user stress and mental demands. Such user pushes a stent along using the displayed geography of the arteries using an opaque guide wire must mentally plan where the stent will go and directed to desire geometric landing zones. This is performed while periodically puffing or injecting contrast solution in order for the artery to be visualized. It is difficult to have dark contrast solution being distributed while pushing a dark object corresponding to stent. Visualizing the vessel, pushing a stent to a landing zone, pushing contrast to solution to have a view of overall vascular as part of guiding stent to a target zone near a side branch for example is very difficult. On top of the foregoing, turning one's head back and forth between the various screens, where angiography, fluoroscopy, and intravascular can be far away from each other is very difficult to sustain.

Further, the arteries being traversed have undulating branches that are moving in three-dimensions, it is challenging not to lose track of one's reference frame. As a result, losing track of location can result in a geographic miss relative to a target landing zone. This can be compensated for by continuing to puff/push contrast solution. Notwithstanding, that too much contrast is not recommended for various patient classes based on various conditions such as those with kidney issues. The more complex the stent plan, such as a need for two stents or a need to re-balloon an under expanded stent, all contribute to complexity. In turn, a co-registered system offers numerous advantages.

Figure 2:
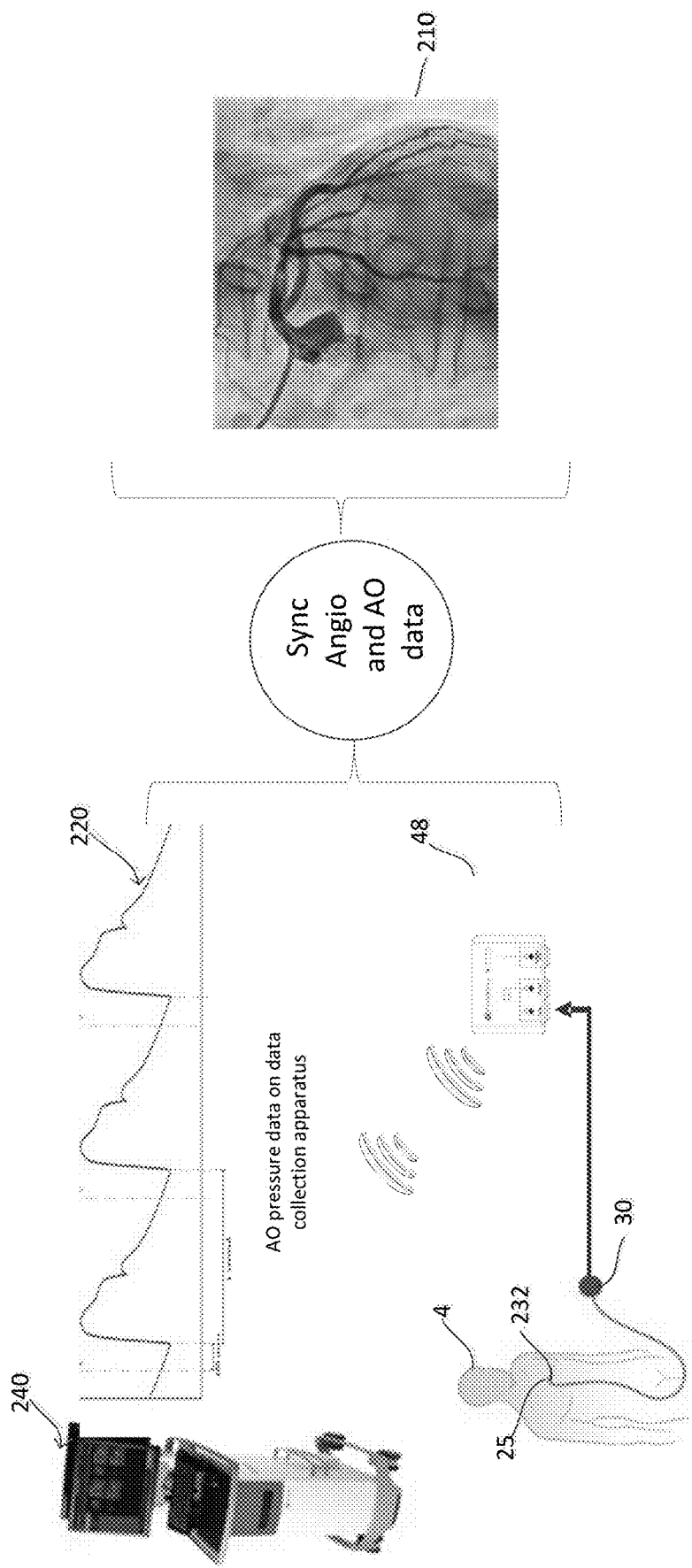
FIG. 2 shows a diagram of synchronizing time-varying heart cycle data of a subject with angiographic images of the subject, in accordance with aspects of the disclosure.

Given that various data collection and diagnostic systems, such as angiography systems that use OCT, IVUS, or other intravascular imaging systems use imaging probes with radiopaque markers to track a given probe, angiography data can be co-registered with intravascular data. Both of these data sets can be co-registered, correlated, or cross-correlated with live fluoroscopy fees using pressure signals used for monitoring aortic pressure or other pressure signals, EKG signals, dicrotic notch signals and location, and other timing signals. A dongle or other data transmitter such as shown in FIG. 2 can transmit pressure data on a given data collection apparatus such as an imaging system or pressure sensing system. A pressure transducer from a subject can relay such pressure data wirelessly or by wired connection to an intravascular imaging system, to synchronize angiography data and such pressure data, and to store such data for use in the cath lab. The foregoing treatment of synchronized pressure data with angiography data can also be achieved with other pressure signals, EKG signals, dicrotic notch signals and location, other timing signals, frames of intravascular data, pressure data, flow data, and other data collected in the cath lab. The data collected can be shown on the live fluoroscopy data.

In one embodiment, about K frames per second for angiography data is split up into K/n slices for a given curve such as AO pressure curve or ECG curve. In one embodiment, K is about 15. For a given angio frame or OCT/IVUS frame the angiography data or OCT/IVUS data can be co-registered relative to bin, time period, slice, or time slice of a give AO plot, ECG plot, systole plot, diastole plot, or other time varying function suitable for co-registration. In one embodiment, a given time varying plot/function such AO curve or ECG plot is divide into K, such as 15, bins. As a result, the co-registration system can track or otherwise map which frame corresponds to a first part of the heart cycle, which frame corresponds to an identified dicrotic notch, which part of frame corresponds to a middle of diastole, etc. Thus a given curve or plot is portioned into bins, subsets, slices, etc. and mapped or linked to frames of angiography and/or intravascular data and/or fluoroscopy data. In one embodiment, the AO pressure near an aortic notch may be preferred as a result of greater stability.

Each heart cycles is about 1 second. Further, a typical angiography imaging system operates at about 15 frames per second. In one embodiment, there are about 15 frames per heart cycle. In one embodiment, there are about 30 frames per heart cycle. The system includes components to sample K frames per heart cycle. In turn, the sampled data can be smoothed or filtered.

In one embodiment, for a given cath lab data collection system and method embodiment, a live fluoroscopy feed is present. The AO pressure data or other timing or signal data such as ECG is used to determine what part of heart cycle corresponds to a given AO pressure data. This may correspond to identifying systole and diastole in heart cycle or other trackable time periods relative to a heart cycle. Once the AO pressure data or other timing data or signals is mapped to heart cycle or other clock or timing subsystem, then data of interest is co-registered with pre-computed angiography data that has been co-reg with OCT/IVUS markers. In general, the systems and methods identify what part of the heart cycle tracks or corresponds with a particular frame of image data or other parameter of interest.

The foregoing is useful when co-registering live fluoroscopy data. Specifically, a real time correlation is used that effectively identifies the part of the heart cycle that can be tracked over time relative to AO pressure data or other data or signals such ECG data for fluoroscopy data. As a result, this facilitates selecting any frame from set of angiography image frames and replacing such an angiography frame with a live fluoroscopy frame. A frame mapping or replacement can be used or a picture in picture representation can be used as well as others. In one embodiment, a transform or other methodology is used to swap angiography frames with fluoroscopy frames. Various interlacing techniques can be used. This frame swapping supports using a library of images from angiography that were previously generated with contrast.

Given the knowledge of where the images are in time from fluoroscopy relative to the heart cycle, the library of previously generated angiography frames can be interlaced with live frames and vice versa. In this way, the use of contrast solution can be reduced because new angiography frames are not needed to the same degree. The interlacing of live fluoroscopy feed with a library of previously acquired angiography frames from different points in time can be done automatically.

There are numerous benefits to these co-registrations based on heart cycle and other timing correlations. For example, it is possible to push a stent through vasculature for deploying by effectively simulating contrast flushing given the ability to use a library of frames where flushing was previously used in captured angiography frames or using intravascular data such as OCT or IVUS image data. In this way, the systems and methods facilities a reduction in contrast solution exposure and may be obviated by using intravascular image data or at least greatly lessen the need for contrast solution. In various embodiments, the angle/position of imager for fluoroscopy can be changed to help reduce need for contrast solution.

In one embodiment, during an intravascular pullback image frames are dark under angiography. There is a discrete period of time for pullback, which can be tracked and indexed relative to angiography frames and registered relative to AO pressure data, ECG data, dicrotic notch, or other timing data. In one embodiment, every subsequent interlacing of frames can be performed using AO data or other timing data. One or more displays can be used to show live fluoroscopy data using a frame grabber to pull frames from live feed and interlace with angiography frames or combine with intravascular data. Effectively, live fluoroscopy data can be shown and then swapped relative to non-live angiography data, such from a library of angiography frames. Intravascular imaging markers such as OCT/IVUS markers and other information can be combined with, overlaid upon or otherwise used with live fluoroscopy feed. This fusing or combining of various types of image data with live fluoroscopy data can be used to support various outcomes such as accurately knowing where the stent landing zone is positioned.

These techniques and others disclosed herein can also be used to guide an artherectomy balloon, show calcium and other detected elements using intravascular data in live fluoroscopy data streams. Guidewires, stents, side branches, lumen, MLA, lumen diameter, lumen profile, areas, cross-sections, volumes, malapposition, stent under inflation, jailed side branches and other information detectable using intravascular data can be co-registered with live fluoroscopy using the systems and methods disclosed herein.

FIG. 1A shows a system 5 which includes various data collection subsystems suitable for collecting data or detecting a feature of or sensing a condition of or otherwise diagnosing a subject 4. In one embodiment, the subject is disposed upon a suitable support 19 such as table bed to chair or other suitable support. Typically, the subject 4 is the human or another animal having a particular region of interest 25.

The data collection system 5 includes a noninvasive imaging system such as a nuclear magnetic resonance, x-ray, computer aided tomography, or other suitable noninvasive imaging technology. As shown as a non-limiting example of such a noninvasive imaging system, an angiography system 21 such as suitable for generating cines is shown. The angiography system 21 can include a fluoroscopy system. Angiography system 21 is configured to noninvasively image the subject 4 such that frames of angiography data, typically in the form of frames of image data, are generated while a pullback procedure is performed using a probe 30 such that a blood vessel in region 25 of subject 4 is imaged using angiography in one or more imaging technologies such as OCT or IVUS, for example.

The angiography system 21 is in communication with an angiography data storage and image management system 22, which can be implemented as a workstation or server in one embodiment. In one embodiment, the data processing relating to the collected angiography signal is performed directly on the detector of the angiography system 21. The images from system 20 are stored and managed by the angiography data storage and image management 22. Other imaging systems disclosed herein can replace or augment system 21.

Imaging data and data derived therefrom, such as blood vessel representations are generated and displayed as part of a user interface to expeditiously provide diagnostic information. These can take the form of different lumen profiles and ratios of values at corresponding positions along their length such as areas, diameters, or other geometric values.

The system of FIG. 1A includes various components for imaging one or more arteries and/or components of the cardiovascular system using one or more of CT scan, ultrasound, IVUS, X-ray-based imaging modalities, magnetic resonance imaging, optical coherence tomography, infrared, laser-based imaging, and other imaging modalities for intravascular and extravascular imaging. In one embodiment system server 50 and/or workstation 85 can handle the functions of system 22. In one embodiment, the entire system 5 generates electromagnetic radiation, such as x-rays. The system 22 also receives such radiation after passing through the subject 4. In turn, the data processing system 22 uses the signals from the angiography system 21 to image one or more regions of the subject 4 including region 25.

The region of interest 25 may be a subset of the vascular or peripherally vascular system such as a particular blood vessel. This subset can be imaged using OCT, ultrasound, alone or combination or one of the other imaging modalities disclosed herein. In one embodiment, this region of interest may include a stent or a region at which a stent is to be placed. The stent can be imaged at different points in time such as after deployment and after supplemental stent expansion.

A catheter-based data collection probe 30 is introduced into the subject 4 and is disposed in the lumen of the particular blood vessel, such as for example, a coronary artery. A probe or other device that includes a balloon can also be used to increase the level of stent expansion in response to detecting stent under expansion using one or more imaging modalities.

The probe 30 can be a variety of types of data collection probes such as for example an OCT probe, an FFR probe, an IVUS probe, a probe combining features of two or more of the foregoing, and other probes suitable for imaging within a blood vessel. In one embodiment, a balloon delivery device is moved along guidewire used for the imaging probes disclosed herein. In one embodiment, the probe 30 typically includes a probe tip, one or more radiopaque markers, an optical fiber, and a torque wire. Additionally, the probe tip includes one or more data collecting subsystems such as an optical beam director, an acoustic beam director, a pressure detector sensor, other transducers or detectors, and combinations of the foregoing.

For a probe that includes an optical beam director, the optical fiber 33 is in optical communication with the probe with the beam director. The torque wire defines a bore in which an optical fiber is disposed. In FIG. 1A, the optical fiber 33 is shown without a torque wire surrounding it. In addition, the probe 30 may also include a sheath such as a polymer sheath (not shown) which forms part of a catheter. The optical fiber 33, which in the context of an OCT system is a portion of the sample arm of an interferometer, is optically coupled to a patient interface unit (PIU) 35 as shown.

The patient interface unit 35 includes a probe connector suitable to receive an end of the probe 30 and be optically coupled thereto. Typically, the data collection probes 30 are disposable. The PIU 35 includes suitable joints and elements based on the type of data collection probe being used. For example a combination OCT and IVUS data collection probe requires an OCT and IVUS PIU. The PIU 35 typically also includes a motor suitable for pulling back the torque wire, sheath, and optical fiber 33 disposed therein as part of the pullback procedure. In addition to being pulled back, the probe tip is also typically rotated by the PIU 35. In this way, a blood vessel of the subject 4 can be imaged longitudinally or via cross-sections. The probe 30 can also be used to measure a particular parameter such as a fractional flow reserve (FFR) or other pressure measurement.

In turn, the PIU 35 is connected to one or more intravascular data collection systems 42. The intravascular data collection system 42 can be an OCT system, an IVUS system, another imaging system, and combinations of the foregoing. For example, the system 42 in the context of probe 30 being an OCT probe can include the sample arm of an interferometer, the reference arm of an interferometer, photodiodes, a control system, and patient interface unit. Similarly, as another example, in the context of an IVUS system, the intravascular data collection system 42 can include ultrasound signal generating and processing circuitry, noise filters, rotatable joint, motors, and interface units. In one embodiment, the data collection system 42 and the angiography system 21 may have a shared clock or other timing signals configured to synchronize angiography video frame time stamps and OCT image frame time stamps.

Various extravascular imaging systems such as angiography systems can image a given region of interest such as a stent in various states of expansion. The extravascular imaging data can be co-registered with the intravascular imaging data. The outputs of the intravascular and the extravascular imaging modalities can be displayed relative to patient in cath lab using a graphical user interface 127 on various displays 123, as shown in FIG. 1B.

In addition to the invasive and noninvasive image data collection systems and devices of FIG. 1A, various other types of data can be collected with regard to region 25 of the subject and other parameters of interest of the subject. For example, the data collection probe 30 can include one or more pressure sensors such as, for example, pressure wire 232 shown in FIG. 2. A pressure wire can be used with or without the additions of OCT or ultrasound components. Pressure readings can be obtained along the segments of a blood vessel in region 25 of the subject 4.

Such readings can be relayed either by a wired connection or via a wireless connection. As shown in a fractional flow reserve FFR data collection system, a wireless transceiver 48 may be configured to receive pressure readings from the probe 30 and transmit them to a system to generate FFR measurements or more locations along the measured blood vessel. One or more displays 82, 83, 123 of FIGS. 1A and 1B, can also be used to show an angiography frame of data, an OCT frame, user interfaces for OCT and angiography data and other controls and features of interest.

As shown in FIG. 1A, The intravascular image data such as the frames of intravascular data generated using the data collection probe 30 can be routed to the data collection processing system 42 coupled to the probe via PIU 35. The noninvasive image data generated using angiography system 22 can be transmitted to, stored in, and processed by one or more servers or workstations such as the co-registration server 50 workstation 85. A video frame grabber device such as a computer board configured to capture the angiography image data from system 22 can be used in various embodiments.

In one embodiment, the server 50 includes one or more co-registration software modules 67 that are stored in memory 70 and are executed by processor 80. The server 50 can include other typical components for a processor-based computing server. Alternatively, more databases such as database 90 can be configured to receive image data generated, parameters of the subject, and other information generated, received by or transferred to the database 90 by one or more of the systems devices or components shown in FIG. 1A. Although database 90 is shown connected to server 50 while being stored in memory at workstation 85, this is but one exemplary configuration. For example, the software modules 67 can be running on a processor at workstation 85 and the database 90 can be located in the memory of server 50. The device or system used to run various software modules are provided as examples. In various combinations the hardware and software described herein can be used to obtain frames of image data, process such image data, and register such image data.

As otherwise noted herein, the software modules 67 can include software such as preprocessing software, transforms, matrices, and other software-based components that are used to process image data or respond to patient triggers to facilitate co-registration of different types of image data by other software-based components 67 or to otherwise perform such co-registration. The modules can include lumen detection using a scan line based or image based approach, stent detection using a scan line based or image based approach, indicator generation, stent expansion evaluation and assessment, stent landing zone detection and indication for deployed stents; angiography and intravascular imaging co-registration, and other modules supportive and programmed to perform the methods disclosed herein.

The database 90 can be configured to receive and store angiography image data 92 such as image data generated by angiography system 21 and obtained by the frame grabber server 50. The database 90 can be configured to receive and store OCT/IVUS image data 95 such as image data generated by OCT system 42 and obtained by the frame grabber server 50.

In addition, the subject 4 can be electrically coupled via one or more electrodes to one more monitors such as, for example, monitor 49. Monitor 49 can include without limitation an electrocardiogram monitor configured to generate data relating to cardiac function and showing various states of the subject such as systole and diastole. Knowing the cardiac phase can be used to assist the tracking of vessel centerlines, as the geometry of the heart, including the coronary arteries, is approximately the same at a certain cardiac phase, even over different cardiac cycles.

The use of arrow heads showing directionality in a given figure or the lack thereof are not intended to limit or require a direction in which information can flow. For a given connector, such as the arrows and lines shown connecting the elements shown in FIG. 1A, for example, information can flow in one or more directions or in only one direction as suitable for a given embodiment. The connections can include various suitable data transmitting connections such as optical, wire, power, wireless, or electrical connections.

One or more software modules can be used to process frames of angiography data received from an angiography system such as system 22 shown in FIG. 1A. Various software modules that can include without limitation software, a component thereof, or one or more steps of a software-based or processor executed method can be used in a given embodiment of the disclosure.

The systems of FIGS. 1A and 1B are suitable for displaying intravascular and extravascular image data. In particular, the systems are advantageous for stent planning and assessment of stent expansion and target stent expansion assessment. In one embodiment, a stent expansion threshold can be provided by the diagnostic system, such as an OCT, IVUS, or other image data collection system, or such a threshold can be adjusted and set by an end user via a user interface. In one embodiment, the stent expansion threshold used to identify regions of stent under inflation range from about 80% to about 90%. Thus, if a stent is inflated at a first location along its length to a level of 48% it is tagged or represented with one visual cue or indicia, while if at another region the stent is expanded to a level at or above the threshold it is identified with another visual cue or indicia.

FIG. 1B shows a cath lab set up with components of an imaging and data collection system, such as system of FIG. 1A for performing OCT, FFR, IVUS, angiography, CT scans or other types of imaging, measurement and assessment for one or more arteries of a patient. A user can interact with the data collection system or otherwise access and display stored image data through the various displays shown. Exemplary user interfaces showing intravascular imaging data and stent expansion data co-registered with angiography data is displayed. A support member 115 such as an accessory rail on a table, bed or other support 120. The support member 115 can be part of the support 120 and a controller can attach directly to the support 120 in one embodiment.

In one embodiment, the controller can include any suitable input device and can be used to navigate user interface screens and parameters such as target stent expansion values and other stent expansion thresholds. The controller can be used to display and navigate a graphical user interface displayed on one or more monitors or displays 123. In one embodiment, the monitors can be mounted on a ceiling suspension. A graphical user interface 127 can be displayed on a given monitor. The graphical user interfaces may include stent expansion and co-registered intravascular data, such as OCT/IVUS data, angiography data, and fluoroscopic image data.

In one embodiment, the controller has a feature set configured to map to commands and menus available to a user as part of the graphical user interface 127. An angiography system or other imaging system disclosed herein 125 can be positioned relative to the support 120 to obtain x-rays of the patient while another data collection procedure such as an OCT/IVUS procedure is underway. The graphical user interface 127 can display such OCT, angiography, FFR, IVUS, and other data of interest to a user. The controller is configured to control the interface 127 and navigate the menus and image display features it presents to a user. Co-registering the angiography data with intravascular imaging can support assessment of stent expansion levels. In turn, co-registering fluoroscopy with angiography and intravascular imaging improves upon stent deployment and facilitates only needing to look at one display during an artery-directed treatment such as stenting, artherectomy, angioplasty, etc.

The disclosure describes systems and methods to depict regions of stent under expansion and at a target expansion level relative to a representation of a blood vessel generated using intravascular data to facilitate targeted balloon placement and sizing relative to placed stent. Optical coherence tomography and other imaging modalities can be used to generate various blood vessel representations and to perform various image data processing technique to detect and/or visually represent the lumen L, stent struts SS, side branches SB, and others as shown and described herein.

These systems, devices, and methods may be implemented when a subject is first evaluated using a diagnostic method such as one or more cardiac imaging modalities. These imagining modalities can include, without limitation, OCT, IVUS, computer aided tomography, MRI, angiography, x-rays, pressure data-based models of heart and/or blood vessel operation and status.

FIG. 2 shows angiography data, such as angiographic image 210, that are synchronized with time-varying parameter of a patient's cardiac system using data collected from region 25 of patient 4 using the system described in FIGS. 1A and 1B. The collected cardiac data may include ECG data or AO pressure data 220 that is acquired by pressure wire 232 of probe 30 and transmitted by wireless transceiver 48 to data collection apparatus 240. AO pressure data 220 a time varying parameter that can be synchronized with angiography data acquired from the patient. For example, angiographic image 210 can be synchronized with a portion of the AO data 220 by determining the portion of the AO pressure data 220 that corresponds to the time at which angiographic image 210 was captured. This process can be performed for a plurality of angiographic images, so that each angiographic image is correlated with a particular portion of the patients AO pressure data 220, based on the time at which both the angiographic image and the AO pressure data 220 were obtained.

Figure 3:
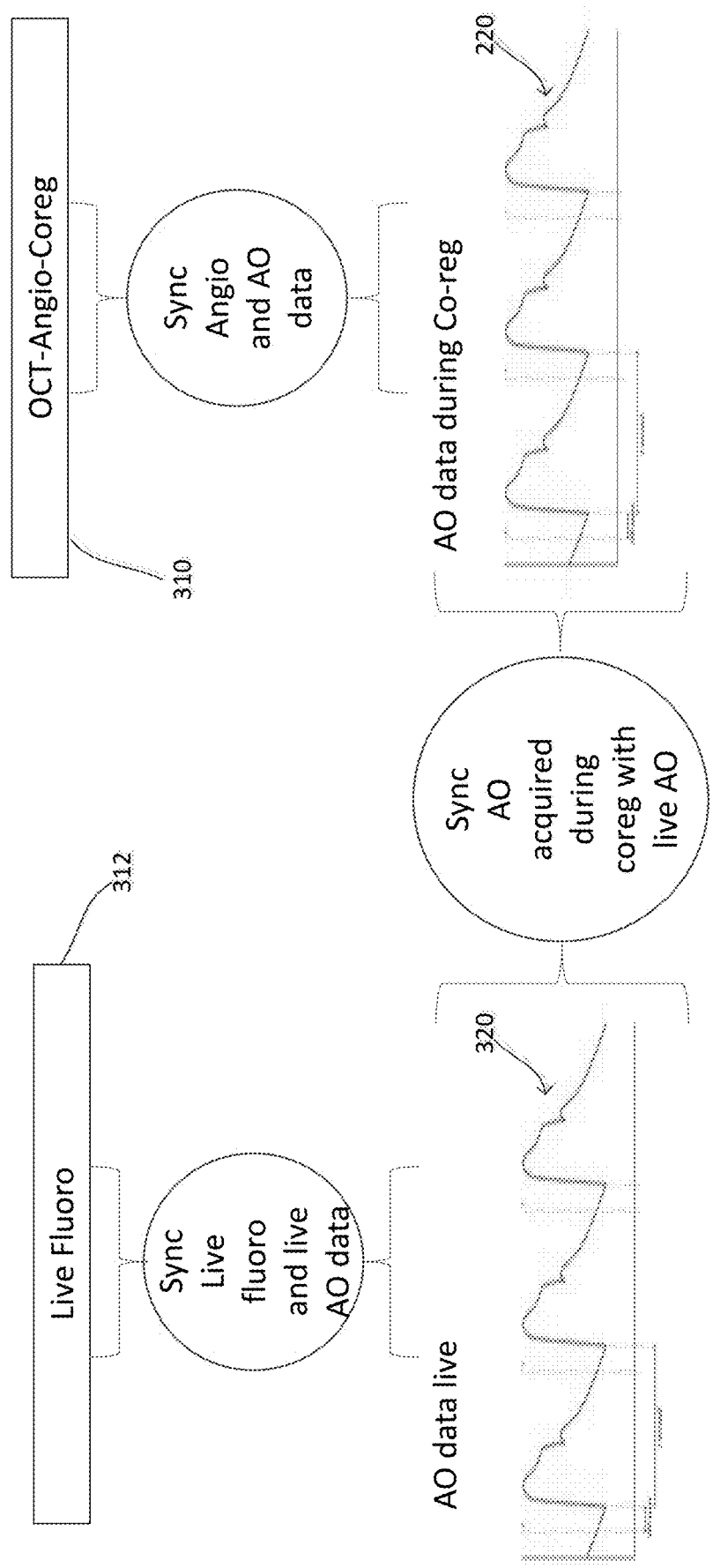
FIG. 3 shows a diagram of synchronizing live data and non-live data in accordance with aspects of the disclosure.

In FIG. 3, intravascular (OCT/IVUS) and angiography data 310 are obtained and co-registered together. Similar to the synchronization described in connection with FIG. 2, the co-registered intravascular/Angiographic data 310 is synchronized relative to the AO data 220, so that particular angiographic and OCT/IVUS images are correlated with particular portions of the AO data 220. The synchronized intravascular/Angiographic data 310 and AO data 220 can be stored in one or more storage devices described in FIGS.

1A and 1B. In addition, the system of FIGS. 1A and 1B may collect live fluoroscopic images 312 from the patient. These live fluoroscopic images 312 can be synchronized with live AO data 320. Although AO data is used as an example, the synchronization described herein may be performed with any repeating, time-varying data obtained during the live image and initial co-registration stages, including ECG data. The live AO data 320 can then be compared to and synchronized with the previously-obtained AO data 220. In turn, the live fluoroscopy data 312 may be synchronized or co-registered with the intravascular-angiography data 310 based on this comparison. In this way, corresponding fluoroscopic images and angiographic images can be identified in connection with particular subsets of the patient's heart cycle.

Figure 4A:
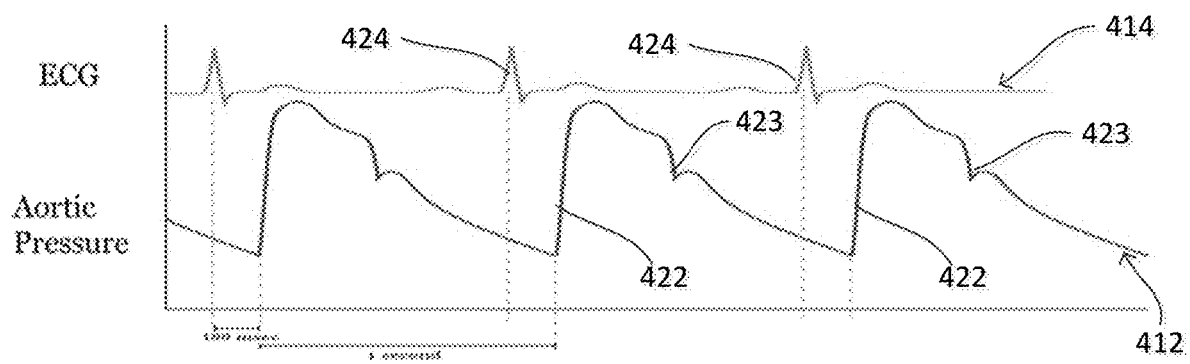
FIGS. 4A and 4B shows a diagram of correlating time-varying heart cycle signal data with angiographic images in accordance with aspects of the disclosure.

In various embodiments, ECG and AO pressure signals are used to identify the angiography frames that correspond to each part of the heart cycle. As shown in FIG. 4A, ECG pulses 424 can be identified in the patient's ECG signal 414, while AO pressure rises 422 and dicrotic notches 423 can be identified in the patient's AO pressure signal 412. ECG signals 414 and AO pressure signals 412 obtained during intravascular imaging and angiography imaging are synchronized to the captured image data sets. As discussed above, the ECG and AO pressure signals obtained during initial co-registrations of the intravascular-Angiographic images can be synchronized with live ECG and AO pressure signals to in turn synchronize live fluoroscopy images with the initially co-registered intravascular and angiography images. The grid of vertical lines 430 in FIG. 4B, corresponds to time slices or bins of heart cycle that are tied to parts of the ECG signal 414 and AO signal 412, all of which are correlated with particular angiographic image frames 442-448. For example, angiography image frame 442 was obtained during the time period in which AO pressure signal 412 increases from a signal minimum toward a signal maximum. Thus, angiographic image frame 442 is identified as being associated with this portion of the AO pressure signal 412. Angiographic image frames 444 and 446 were obtained during the beginning and ending periods, respectively, of a dicrotic notch within AO pressure signal 412. Similarly, angiographic image frame 448, which was obtained during an ECG pulse, is associated with the corresponding time period represented in ECG signal 414. This process may be performed for every intravascular and angiographic image that is obtained, so that each intravascular-angiographic image is correlated to a particular time period within the patient's heart cycle.

Figure 4B:
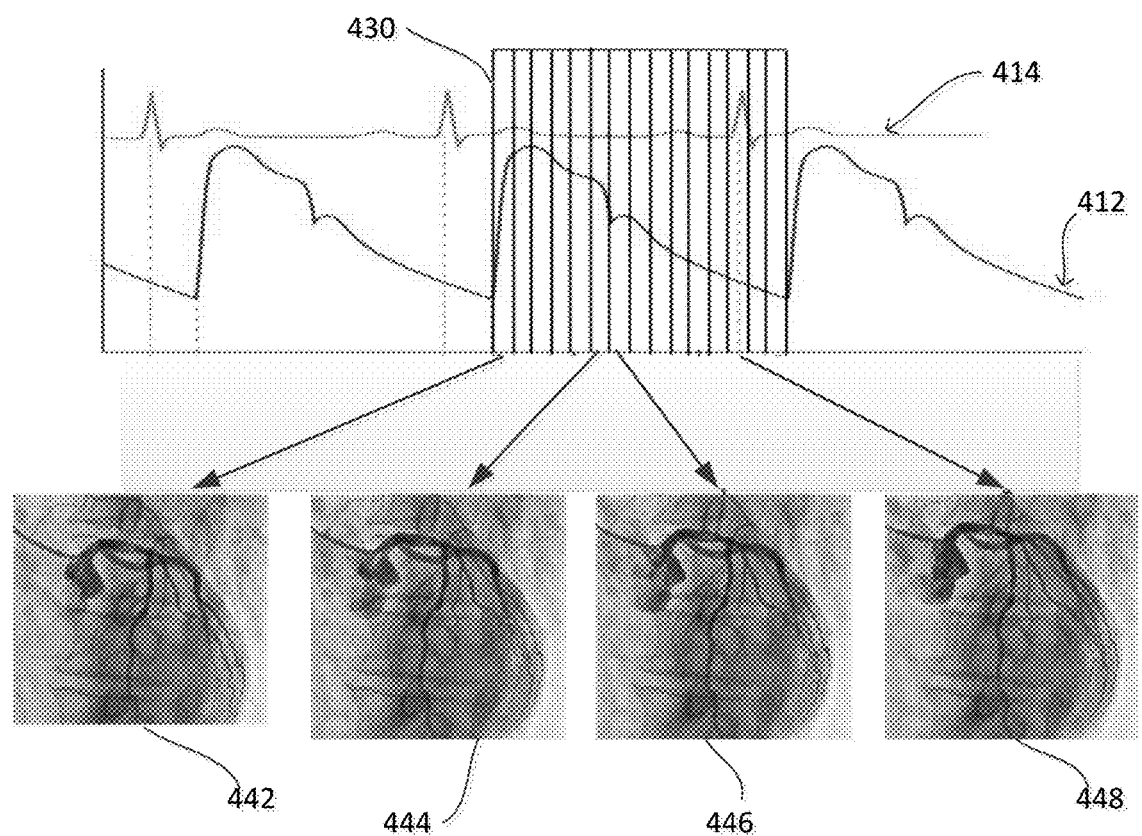

While FIG. 4B shows a single heart cycle being broken down into a series of time slices, the same division may be performed in connection with a plurality of heart cycles. In addition, the number of time slices may vary. For example, the system described in FIGS. 1A and 1B may be configured to capture OCT/IVUS images and angiographic images at a variety of frame rates, and these frame rates may be configured by the user. For example, the disclosed system may be configured by the user to capture angiographic images at either 15 frames per second or 30 frames per second. Similarly, the disclosed system may be configured to divide the ECG and AO pressure signals into time slices of varying duration. If the ECG and AO pressure signals are divided into 30 time slices per second and the angiographic images are captured at 30 frames per second, then the system can be configured to correlate one angiographic image with each time slice. If the ECG and AO pressure signals are divided into 15 time slices per second, and the angiographic images are captured at a rate of 30 images per second, then multiple angiographic images can be assigned to a particular time slice. Likewise, if the number of time slices are greater than the number of captured angiographic images during a particular period of time, then only some time slices will be correlated with an angiographic image. As discussed above, the angiography frames may also be co-registered with OCT or other intravascular images obtained at the same time based on marker locations in the intravascular images and timing systems used between the two imaging modalities.

Figure 5:
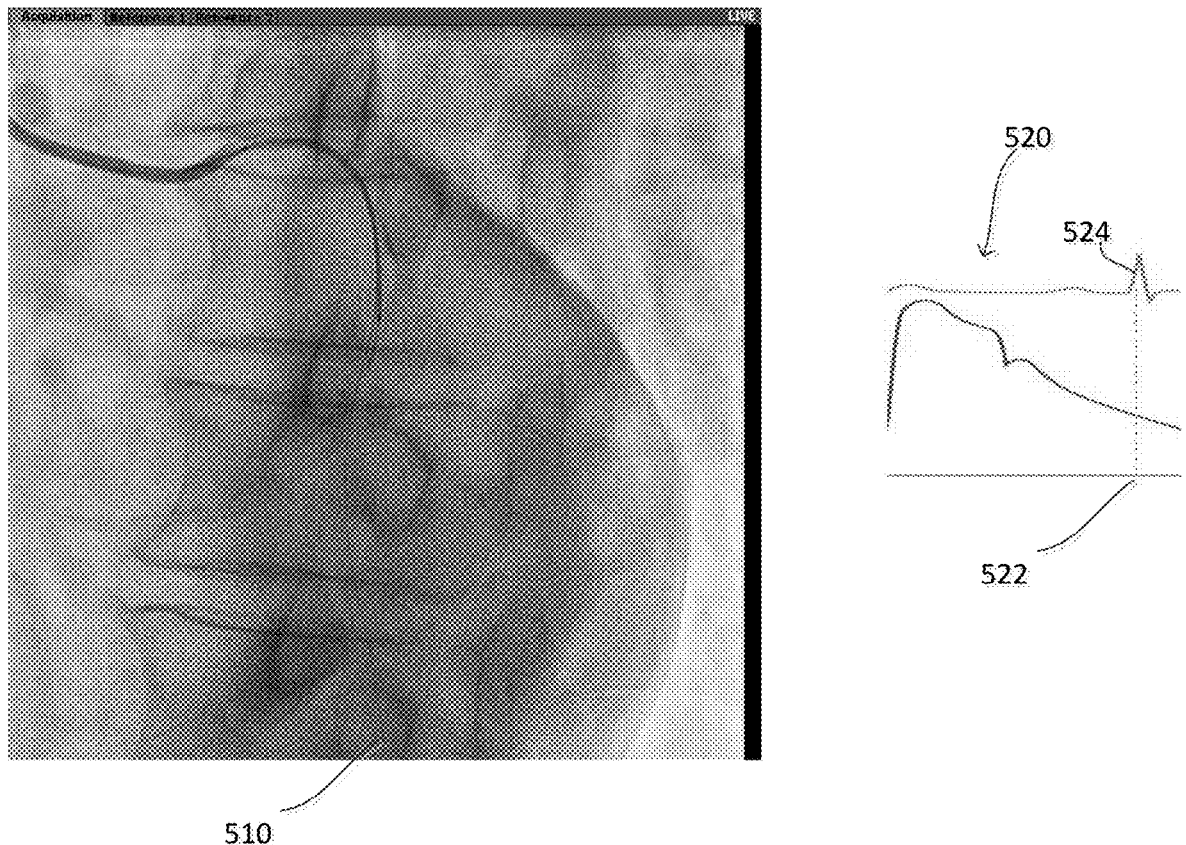
FIG. 5 shows a live fluoroscopic image and live time-varying heart cycle signal data of a subject in accordance with aspects of the disclosure.

Once angiographic images have been correlated to particular portions, or time slices, of the patient's heart cycle data, then the disclosed systems and methods may identify angiographic image frames that correspond to live fluoroscopy images, based on real-time correlation with live ECG and AO signals. For example, FIG. 5 shows a live fluoroscopic image 510 and live ECG and AO pressure signals 520, wherein the live fluoroscopic image 510 is correlated to a particular set of ECG and AO pressure signals that are being simultaneously being obtained at time 522. This live ECG and AO pressure signal 520 can also be correlated with the previously obtained ECG and AO signals to support correlating and co-registered the live fluoroscopic image 510 with a library of OCT/IVUS and angiography images that have been previously obtained. For example, the disclosed system may identify one or more angiographic images that were previously captured during the same portion of the patient's heart cycle as the live fluoroscopic image 510, which is determined based on the ECG and AO pressure data. Thus, the disclosed system may track the ECG and AO signals for the live fluoroscopic image and identifying corresponding ECG and AO signals for the previously captured intravascular and angiographic images.

Figure 6:
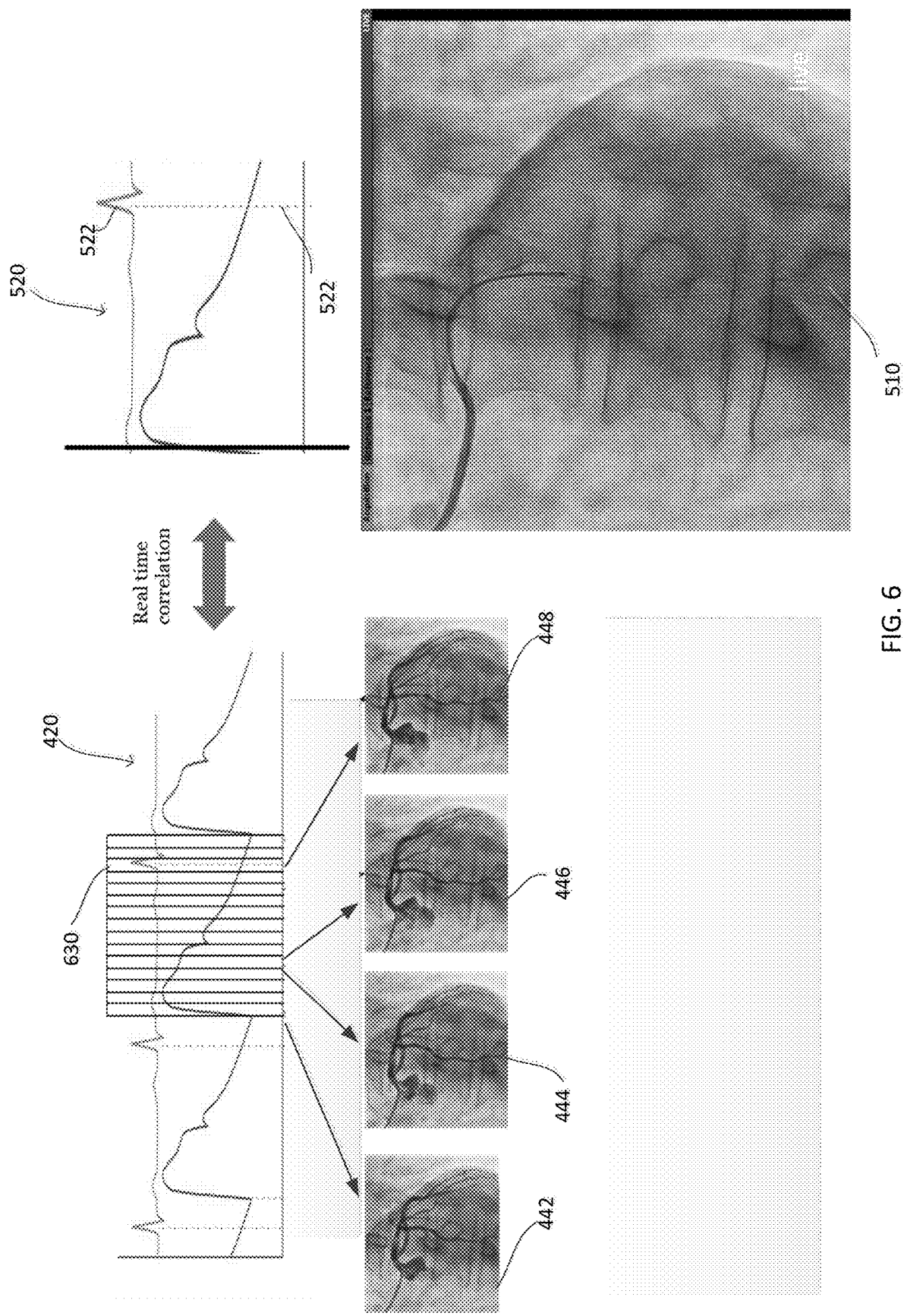
FIG. 6 shows a diagram of real time correlation between non-live data and live data in accordance with aspects of the disclosure.

For example, the time slices 430 of ECG signal 414 and AO signal 412 shown in FIG. 4B can be correlated to the ECG and AO signals 520 shown in FIG. 5. As shown in FIG. 6, the time slice 630 for ECG and AO pressure signals 420 is determined to correspond to the ECG and AO signals 520 at the time 522, as they both represent the portion of the patient's heart cycle in which the corresponding ECG pulse occurs. In this way, the disclosed system determines that angiographic image 448 corresponds to the same portion of the patient's heart cycle as live fluoroscopic image 510. Based on this identified correlation with previously obtained ECG and AO pressure signals 420, the live ECG and AO signals 520 can act as a timing signal onto which the non-live data can be mapped, including, the previously captured OCT and angiographic image data. Thus, angiographic images 442-448 for various time slices may be correlated to a corresponding portion of the live ECG and AO signals 520.

Figure 7:
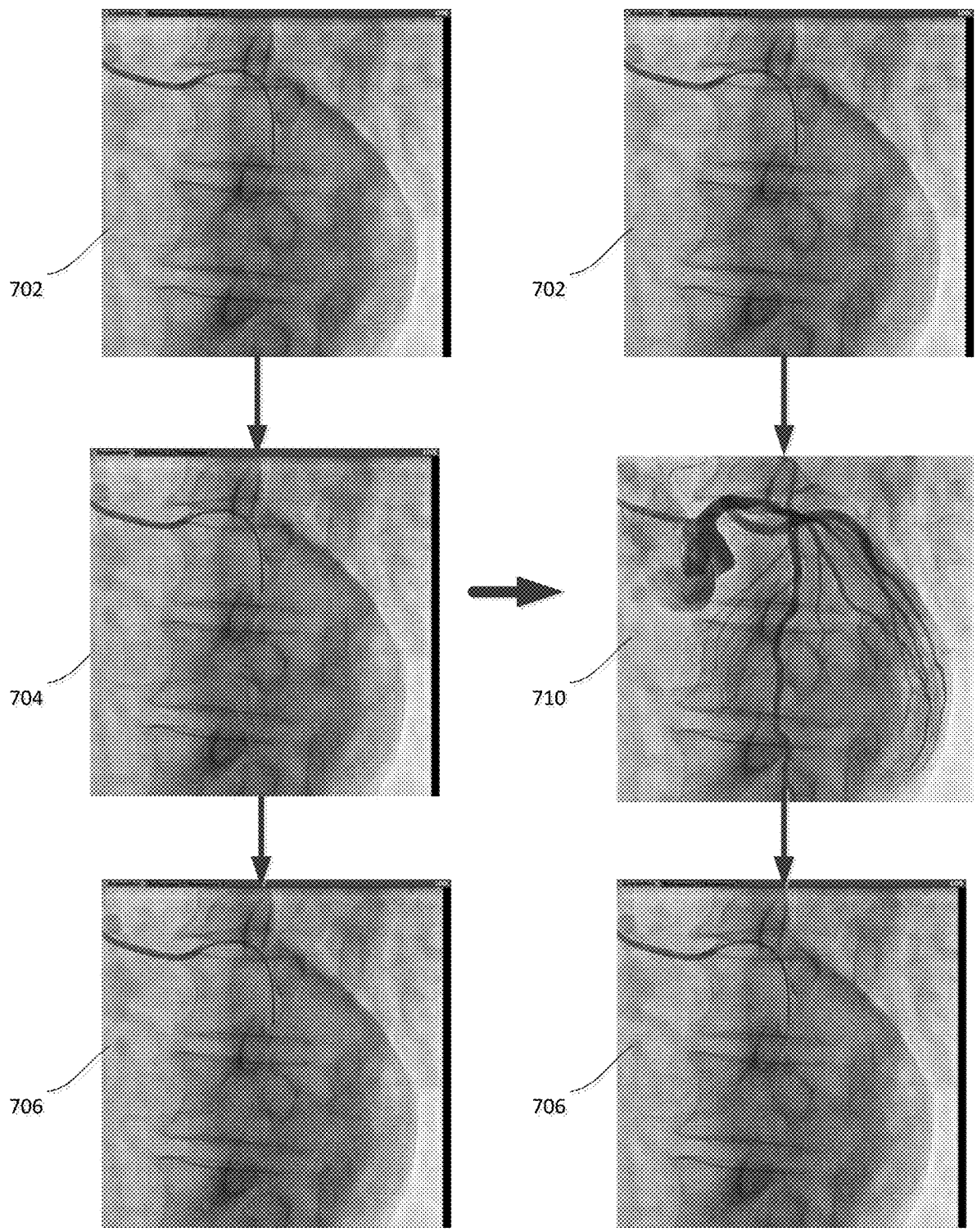
FIG. 7 shows the replacement of a live fluoroscopic image with a non-live angiographic image in accordance with aspects of the disclosure.
Figure 8:
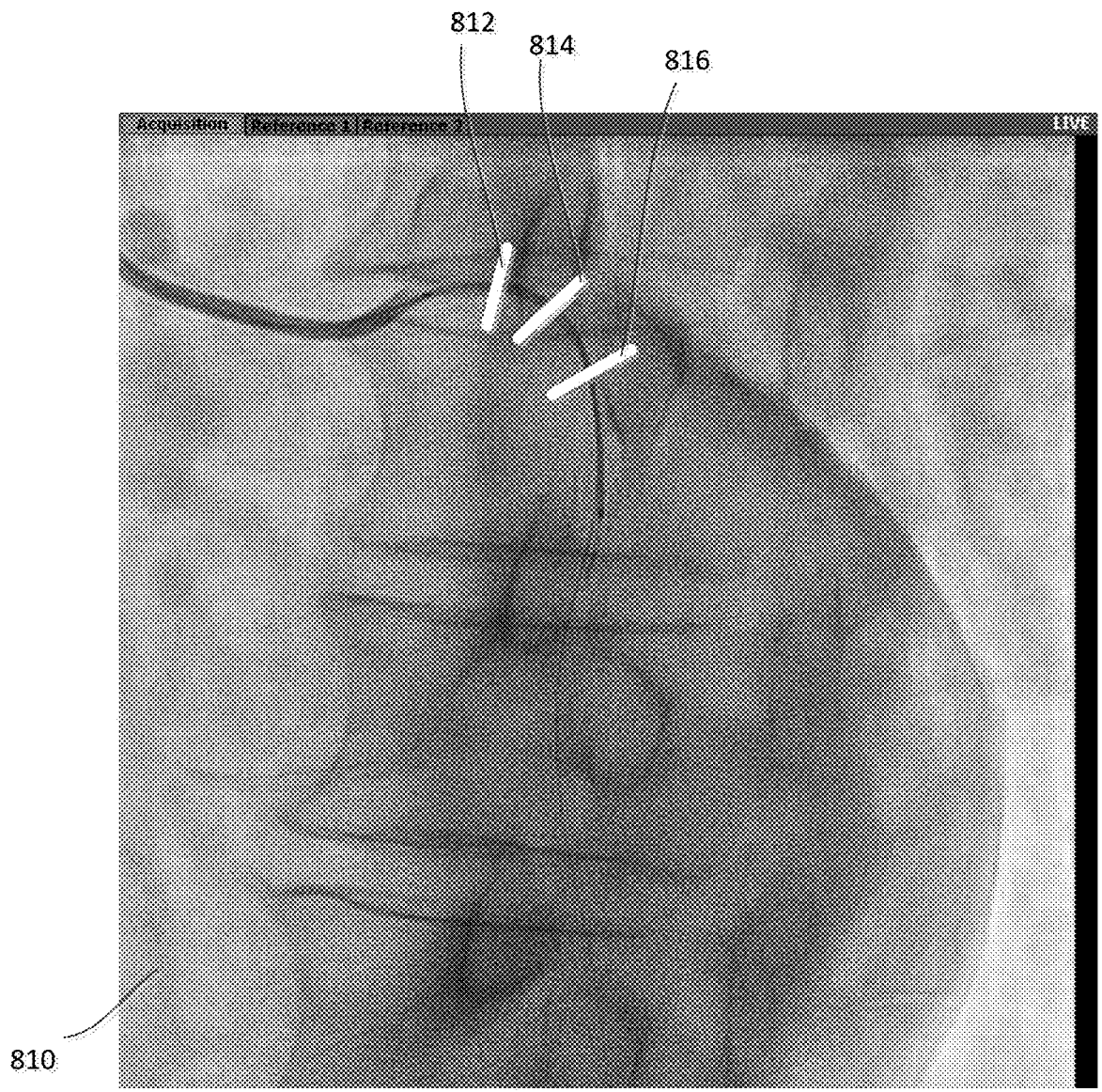
FIG. 8 shows a live fluoroscopic image that has been overlaid with markers in accordance with aspects of the disclosure.

Based on the correlation of non-live and live signals described above, angiographic image frames can be combined with live fluoroscopy to reduce contrast solution usages. For example, FIG. 7 shows a series of live fluoroscopic image frames 702, 704, and 706, wherein fluoroscopic image frame 704 has been replaced in real time with an angiographic image frame 710. As described above, the disclosed system identifies, based on the patient's cardiac signals, that angiographic image frame 710 corresponds to the same portion of the patient's heart cycle as live fluoroscopic image frame 704. In this way, the doctor may be presented with both angiographic images and fluoroscopic images within a single series of image frames. In this way, the doctor may be able to better track various instruments and stent locations within the live fluoroscopic image by using the previously captured angiographic image as a reference. While FIG. 7 shows a fluoroscopic image 704 being replaced with angiographic image 710, the interlacing of angiographic images may occur without the removal of any live fluoroscopic image frames. For example, one or more angiographic image frames may be inserted in between the live fluoroscopic image frames, so as to present the combined frames at a higher frame rate. Alternatively, one or more live fluoroscopic image frames may be replaced by one or more corresponding angiographic image frames. In addition, the disclosed system may allow a user to select the number of successive fluoroscopic and angiographic images that are to be displayed. For example, the user may configure the system so that it presents a series of three live fluoroscopic image frames followed by two successive angiographic image frames, or the user could configure the system to display one angiographic image within each series of four live fluoroscopic images. The user may also configure the frame rate at which the successive fluoroscopic and angiographic images are shown. In this way, the user is able to control the manner in which successive images of the live fluoroscopic and non-live angiographic images are displayed.

Further, non-live image data may be overlaid onto live fluoroscopic images in accordance with aspects of the disclosure described above. For example, FIG. 7B, shows a live fluoroscopic image 810 that is displayed with stent planning markers 812, 814, and 816 having been overlaid onto the fluoroscopic image. These stent planning makers 812-816 may be based on markers that were placed within a series of angiographic images. The relative location of these markers will move from one angiographic image to another, as the patient's heart cycle will cause various arteries within the heart to move. However, by correlating both the angiographic images and fluoroscopic images to the patient's heart cycle, the stent planning markers 812-814 can be overlaid onto each fluoroscopic image in a manner that maintains their proper position relative to the artery for which the stent is to be placed. Thus, the system provides a more accurate placement of stent planning markers from OCT-Angiographic images on live fluoroscopy feed. These markers and other indicia help reduce geographic miss by ensuring physicians target the region they had planned to address in OCT. Other useful intravascular-Angiographic data can also be overlaid onto the fluoroscopic images without limitation, including data acquired from IVUS images.

Figure 9:
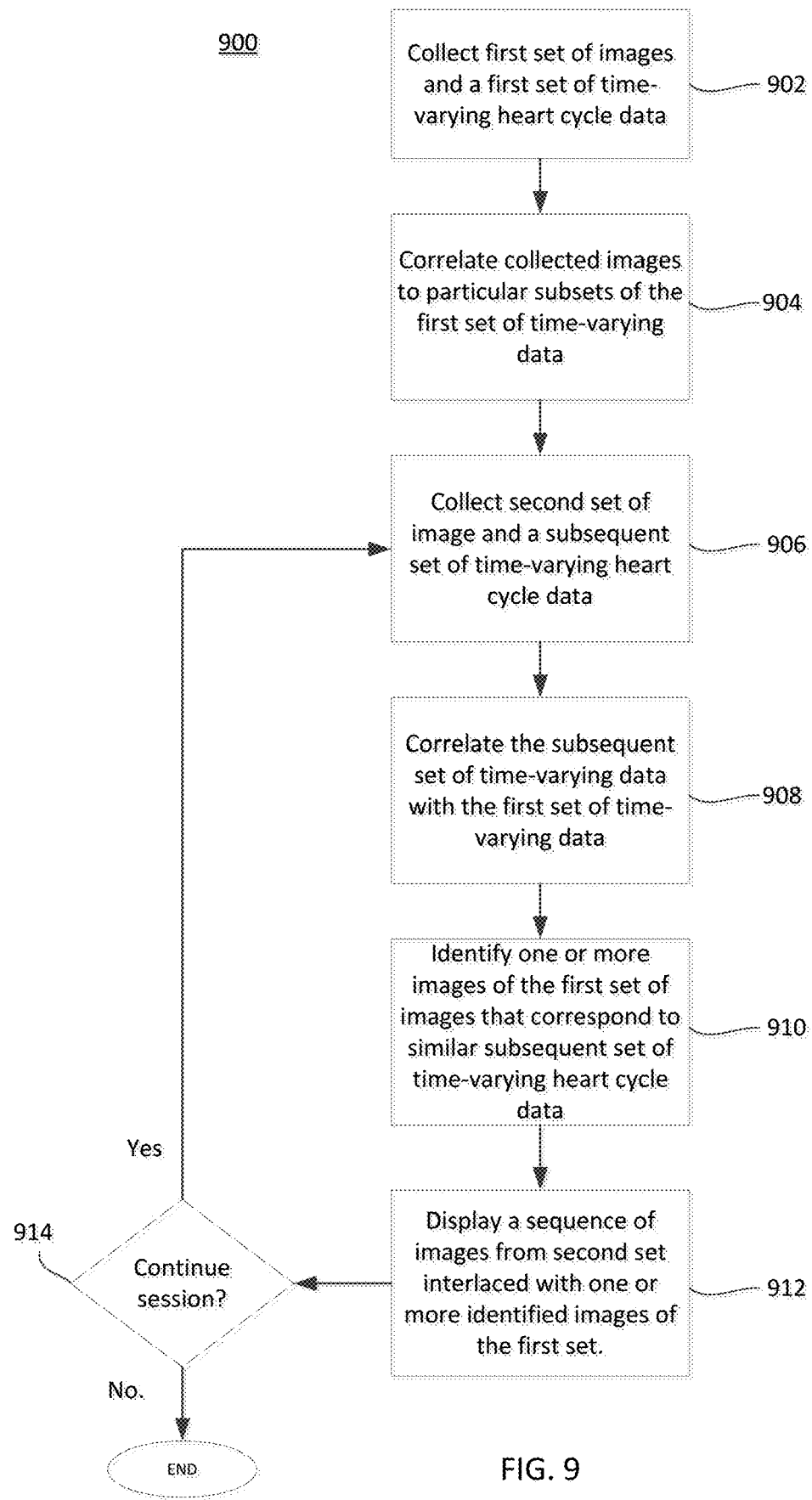
FIG. 9 shows a flow diagram of a method in accordance with aspects of the disclosure.

Flow diagram 900 of FIG. 9 provides an example by which the system shown in FIGS. 1A and 1B may provide a user with a display of interlaced non-live and live images, wherein the images are presented in a sequential order, with both live and non-live images corresponding to the patient's heart cycle. While the operational blocks of FIG. 9 are provided in a particular order, one or more processors of the disclosed system may be configured to add operations, remove operations, or switch the order of the operations in accordance with aspects of the method and system. As provided in Block 902, the system may collect a plurality of a first set of images, as well as a first set of time-varying heart cycle data. As discussed above, the plurality of the first set of images may include angiographic images, along with co-registered intravascular images, such as OCT images or IVUS images. The time-varying heart cycle data may include data representing ECG signals, AO pressure data, or other time-varying data related to the patient's heart cycle, which is collected while the first set of images is being captured. In Block 904, collected first set of images are correlated to particular subsets of the first set of time-varying data. An example of this correlation is shown in FIG. 4B, wherein angiographic images are correlated with time slices of the ECG and AO signal data, based on the time period in which the angiographic image was captured. The correlation of the collected images and time-varying data may include storing the image and time-varying data in a computer storage medium in a manner that identifies a relationship between a particular image and a particular subset of time-varying data. Thus, each image from the first set of images may be correlated with a particular portion of the patient's heart cycle. For Block 906, a second set of images are collected, along with a subsequent set of time-varying heart cycle data. As discussed above, the second set of images may be live fluoroscopic images, which are collected along with live heart cycle data of the patient. This subsequent set of live heart cycle data may be correlated with the first set of time-varying heart cycle data, as provided in Block 908.

As discussed above, the patient's heart cycle contains repeating patterns, such as repeating pressure rises, dicrotic notches, and ECG pulses. These features of the live heart cycle data can be correlated, or matched, with the first set of heart cycle data in accordance with the disclosed systems and methods. In Block 910, the system identifies one or more images of the first set that correspond to similar time-varying heart cycle data as one or more images of the second set. As discussed in connection with FIG. 6, by comparing the live ECG and AO pressure data with the non-live ECG and AO pressure data, the system can identify an angiographic image 448, and co-registered intravascular images, that correspond to a similar period in the patient's heart cycle as the live fluoroscopic image 510.

Returning to flow diagram 900, the system may then display a sequence of images that include images of the second set that are interlaced with one or more images of the first set that also correspond to the same portion of the patient's heart cycle. For example, live fluoroscopic images may be interlaced with non-live angiographic images. As discussed above, the interlacing of the non-live images may include replacing one or more of live fluoroscopic images with a non-live angiographic image, wherein the replaced live fluoroscopic image and the selected non-live angiographic image were each captured during a similar, or corresponding, portion of the patient's heart cycle. The interlacing of non-live images may also consist of inserting, rather than replacing, one or more non-live angiographic images in between the live fluoroscopic images that were captured during a similar portion of the patient's heart cycle, based on the identification that occurred in Block 910. The angiographic images may also be interlaced with the live fluoroscopic images by displaying the corresponding angiographic images as a picture-in-a-picture within a display of the live fluoroscopic images. In addition, the displaying of the interlaced angiographic images may include the display of intravascular images, such as OCT images or IVUS images that have been co-registered with the angiographic images. The co-registered intravascular frames may be displayed on the same monitor or a different monitor than the angiographic and fluoroscopic images, and may appear as a picture-in-a-picture within the fluoroscopic and angiographic images. As provided in Block 914, the system may determine if the patient imaging session is to continue, if so, the system may return to Block 906, where additional images of a second type are collected, along with an additional set of time-varying heart cycle data. If an input is received indicating that the patient imaging session is over, then the process may come to an end.

Non-Limiting Software Features and Embodiments for Implementing Live Fluoroscopy Combined with Other Data Such as Image Data In part, the disclosure relates to computer-based methods, systems and devices for visualizing data relative to live fluoroscopy data. In one embodiment, the disclosure relates to using pre-computed angiographic images interlaced with live fluoroscopic images. Image segmentation can be performed using various techniques such as AI or machine learning and others.

These methods of evaluation can include displaying one or more views of an artery from angiography or intravascular imaging relative to one or more live fluoroscopy image frames. The various fluoroscopy-based methods reduced geographic misses and help facilitate better imaging and artery-directed treatments. In one embodiment, the method is performed automatically. Stents inserted in live fluoroscopy mode can be placed in landing zones planned from OCT/IVUS-Angiography co-registration systems and methods.

The systems and methods disclosed herein can perform various steps as described herein such as evaluating detected stents relative to detected lumen contours, calculating stent expansion, calculating MSA, measuring stent parameters and showing expansion levels of stent at different frames along artery and other features and methods as disclosed herein. In addition, system can include co-registration software for co-registering angiography data and intravascular data to show stent expansion data relative to angiography data. In one embodiment, live fluoroscopy data is interlaced with frames of data from one or more intravascular imaging pullback sessions in which a probe is pulled back through a section of an artery and one or more angiography data collection sessions and one or more co-registration timing signals such as AO pressure, ECG signals, and others as disclosed herein.

The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" "overlaying" or "searching" or "detecting" or "measuring" or "calculating" or "comparing" "generating" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT or IVUS probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating imaging data, detecting lumen borders, detecting stent struts, comparing measured perpendicular distances relative to set thresholds, and otherwise performing image comparison, signal processing, lumen detection, stent detection, and comparison of detected stents, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, IVUS scan data, interferometer signal data, target stent profiles, post-stent deployment lumen profiles and images, interpolated lumen profile views indicative of fully expanded stents, ratios of geometric values of expanded stent-based lumen profile to fully expanded lumen profile, stent expansion level indicia (color, hatching, etc.), highlighting/emphasizing pixel properties, side branch locations, side branch diameters, stent expansion percentages or fractions, pre-stenting FFR values, post-stenting FFR values, and other pre and post stenting values and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" or "substantially" is before a quantitative value, the present teachings also include the specific quantitative value itself, unless specifically stated otherwise. The terms "about" and "substantially" as used herein, refer to variations in a numerical quantity that can occur, for example, through measuring or handling procedures in the real world; through inadvertent error in these procedures; through differences/faults in the manufacture of materials, such as composite tape, through imperfections; as well as variations that would be recognized by one in the skill in the art as being equivalent so long as such variations do not encompass known values practiced by the prior art. Typically, the terms "about" and "substantially" means greater or lesser than the value or range of values stated by 1/10 of the stated value, e.g., ±10%.

It should be understood that the order of steps or order for performing certain actions is immaterial so long as the present teachings remain operable. Moreover, two or more steps or actions may be conducted simultaneously.

The use of headings and sections in the application is not meant to limit the disclosure; each section can apply to any aspect, embodiment, or feature of the disclosure. Only those claims which use the words "means for" are intended to be interpreted under 35 USC 112, sixth paragraph. Absent a recital of "means for" in the claims, such claims should not be construed under 35 USC 112. Limitations from the specification are not intended to be read into any claims, unless such limitations are expressly included in the claims.

When values or ranges of values are given, each value and the end points of a given range and the values there between may be increased or decreased by 20%, while still staying within the teachings of the disclosure, unless some different range is specifically mentioned.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method of displaying sets of radiological images of one or more blood vessels of a subject comprising:
   acquiring, by one or more processors, a first set of radiological images of the subject captured during a first time period and a first set of time-varying data that corresponds to a heart cycle of the subject during the first time period;
   correlating, by the one or more processors, subsets of the first set of radiological images with subsets of the first set of time-varying data;
   acquiring, by the one or more processors, a second set of subject radiological images of the subject captured during a second time period and a second set of time-varying data that corresponds to the heart cycle of the subject acquired during the second time period, wherein the second set of radiological images are live radiological images;
   correlating, by the one or more processors, the first set of time-varying data with the second set of time-varying data;
   identifying, by the one or more processors, image frames from the first set of radiological images that corresponds to a subset of the second set of time-varying data;
   generating, by the one or more processors, a live interlaced video that includes the identified image frames from the first set of radiological images interlaced between a plurality of live image frames from the second set of radiological images based on the identified image frames corresponding to the subset of the second set of time-varying data; and
   providing for display, by the one or more processors, the live interlaced video so that the live interlaced video switches between the identified image frames from the first set of radiological images and the plurality of live image frames from the second set of radiological images a plurality of times per second.

2. The method of claim 1, wherein the first set of radiological images are angiographic images and the second set of radiological images are fluoroscopic images.

3. The method of claim 2, wherein the fluoroscopic images are live images of the subject during an intervascular procedure and the second set of time-varying data is live heart cycle data for the subject.

4. The method of claim 1, wherein the first set of time-varying data and the second set of time-varying data include aortic (AO) pressure values.

5. The method of claim 1, wherein the first set of time-varying data and the second set of time-varying data include ECG values.

6. The method of claim 1, further comprises intravascularly imaging the subject during the first time period using an intravascular probe having one or more opaque markers, wherein intravascularly imaging the subject generates a set of intravascular image frames.

7. The method of claim 6 further comprising co-registering the set of intravascular image frames and the first set of radiological images.

8. The method of claim 7 further comprising displaying one or more intravascular image frames or a subset of the one or more intravascular image frames corresponding to one or more of the live image frames.

9. The method of claim 1, wherein generating the live interlaced video comprises replacing one or more of the live image frames from the second set of radiological images with one or more of the identified image frames from the first set of radiological images.

10. The method of claim 9, wherein the identified image frames from the first set of radiological images and the plurality of live image frames from the second set of radiological images are each captured during a corresponding portion of the heart cycle.

11. The method of claim 1, wherein generating the live interlaced video comprises inserting one or more of the identified image frames from the first set of radiological images between the plurality of live image frames from the second set of radiological images.

12. A system for displaying sets of radiological images of one or more blood vessels of a subject comprising:
    a memory for storing image data and time-varying data that corresponds to a heart cycle of a subject; and
    one or more processors in communication with the memory so as to be able to acquire the image data and time-varying data, the one or more processors being operable to:
    acquire a first set of radiological images of the subject captured during a first time period and a first set of time-varying data that corresponds to a heart cycle of the subject during the first time period;
    correlate subsets of the first set of radiological images with subsets of the first set of time-varying data;
    acquire a second set of radiological images of the subject captured during a second time period and a second set of time-varying data that corresponds to the heart cycle of the subject acquired during the second time period;
    correlate the first set of time-varying data with the second set of time-varying data; identify image frames from the first set of radiological images that correspond to a subset of the second set of time-varying data; and
    generate a live interlaced video that includes the identified image frames from the first set of radiological images interlaced between a plurality of live image frames from the second set of radiological images based on the identified image frames corresponding to the subset of the second set of time-varying data; and
    provide for display the live interlaced video so that the live interlaced video switches between the identified image frames from first set of radiological images and the plurality of live image frames from the second set of radiological images a plurality of times per second.

13. The system of claim 12, wherein the first set of radiological images are angiographic images and the second set of radiological images are fluoroscopic images.

14. The system of claim 13, wherein the fluoroscopic images are live images of the subject during an intravascular procedure and the second set of time-varying data is live heart cycle data for the subject.

15. The system of claim 12, wherein the first set of time-varying data and the second set of time-varying data include aortic (AO) pressure values.

16. The system of claim 12, wherein the first set of time-varying data and the second set of time-varying data include ECG values.

17. The system of claim 12, wherein the one or more processors are further operable to intravascularly image the subject using an intravascular probe having one or more opaque markers during the first time period, wherein intravascularly imaging the subject generates a set of intravascular image frames.

18. The system of claim 12, wherein generating the live interlaced video comprises replacing one or more live image frames from the second set of radiological images with one or more of the identified image frames from the first set of radiological images.

19. The system of claim 18, wherein the one or more live image frames from the second set of radiological images and the one or more of the identified image frames from the first set of radiological images represent corresponding portions of the heart cycle.

20. The system of claim 18, wherein the one or more live image frames from the second set of radiological images and the one or more of the identified image frames from the first set of radiological images represent corresponding portions of the heart cycle.

21. The system of claim 12, wherein the one or more processors are further configured to receive user input for adjusting a frame rate of interlaced images from the first set and second set of radiological images.

22. The system of claim 12, wherein the identified image frames from the first set of radiological images are interlaced between the plurality of live image frames from the second set of radiological images in real time, without the removing any of the live image frames from second set of radiological images.

* * * * *